(12) United States Patent
Nguyen et al.

(10) Patent No.: US 6,355,855 B1
(45) Date of Patent: Mar. 12, 2002

(54) PROCESS FOR THE ISOMERIZATION OF 1-ALKENES TO INTERNAL ALKENES AND CATALYST THEREFOR

(75) Inventors: Tuyen T. Nguyen, Wilmington; Brenda A. Lloyd, Newcastle, both of DE (US)

(73) Assignee: Hercules Incorporated, Wilmington, DE (US)

(*) Notice: Subject to any disclaimer, the term of this patent is extended or adjusted under 35 U.S.C. 154(b) by 0 days.

(21) Appl. No.: 09/515,389

(22) Filed: Feb. 29, 2000

(51) Int. Cl.$^7$ ............................... C07C 5/25; C07C 5/23
(52) U.S. Cl. ...................................... 585/670; 585/665
(58) Field of Search ..................... 585/665, 670

(56) References Cited

U.S. PATENT DOCUMENTS

| | | | |
|---|---|---|---|
| 3,439,054 A | 4/1969 | Kroll ........................... | 585/274 |
| 3,641,184 A | * 2/1972 | Smith et al. ................ | 585/665 |
| 4,587,374 A | 5/1986 | Peter ........................... | 585/670 |
| 4,777,314 A | 10/1988 | Provin et al. ............... | 585/512 |
| 4,980,331 A | 12/1990 | Hoxmeier et al. .......... | 502/117 |
| 5,030,606 A | 7/1991 | Klabunde ................... | 502/155 |
| 5,502,018 A | 3/1996 | Chauvin et al. ............ | 502/213 |
| 5,545,792 A | 8/1996 | Cox ............................ | 585/665 |
| 5,723,712 A | 3/1998 | Chauvin et al. ............ | 585/513 |
| 5,789,645 A | 8/1998 | Cox ............................ | 585/665 |

OTHER PUBLICATIONS

Barry et al., J. Chem Soc., Chem. Commun., 177 (1973).
Golden et al., J. Am. Chem. Soc., 86, 5416–5420 (1964).
Cramer, J. Am. Chem. Soc., 88, 2272–2282 (1966).
Casey et al., J. Am. Chem. Soc., 95, 2248–2251 (1973).

* cited by examiner

Primary Examiner—Walter D. Griffin
(74) Attorney, Agent, or Firm—Greenblum & Bernstein, P.L

(57) ABSTRACT

Process for the oligomerization of 1-alkenes to internal alkenes and a catalyst therefor. 1-Alkene is combined, in liquid phase and at a temperature of from about 50 to about 200° C., with a catalyst formed by contacting at least one Group VIII transition metal salt with at least one alkylaluminum compound. If the at least one Group VIII transition metal salt includes cobalt and the at least one alkylaluminum compound includes trialkylaluminum compound the process is carried out in the substantial absence of alkoxyaluminum species. The catalyst for the isomerization of 1-alkene to internal alkene is prepared by combining at least one Group VIII transition metal salt and at least one alkylaluminum compound of the general formula $AlR_aX_b$ in which R represents an alkyl radical, X represents a halogen radical, a is an integer of from 1 to 3, b is 1 or 2, and the sum (a+b) is 3, in a ratio sufficient to provide an atomic ratio of Al in the alkylaluminum compound(s) to Group VIII transition metal(s) of at least about 1:1. If the at least one Group VIII transition metal salt includes cobalt and the at least one alkylaluminum compound includes trialkylaluminum compound the catalyst is substantially free of alkoxyaluminum species.

49 Claims, No Drawings

PROCESS FOR THE ISOMERIZATION OF 1-ALKENES TO INTERNAL ALKENES AND CATALYST THEREFOR

BACKGROUND OF THE INVENTION

1. Field of the Invention

The present invention relates to a process for the oligomerization of 1-alkenes to internal alkenes, particularly 2-alkenes. The present invention also relates to a catalytic composition for the isomerization of 1-alkenes to internal alkenes.

2. Discussion of Background and Other Information

Several processes for the isomerization of alkenes (olefins) are known. For example, alkenes having more than four carbon atoms can be subjected to random isomerization using acids as catalysts, as described, e.g., by Barry et al. in J. Chem. Soc., Chem. Commun. 177 (1973). However, isomerization with acid catalysts is usually accompanied by oligomerization as a side reaction. Isomerization of alkenes can also be achieved by thermal means, i.e., by heating the alkenes. Disadvantages of corresponding processes are the relatively high temperatures necessary for effecting the isomerizations and the numerous side reactions caused thereby. HBr or $I_2$ in the presence of UV light can also induce isomerization of alkenes (see, e.g., Golden et al., J. Am. Chem. Soc., 86, 5416 (1964)). Such processes involve highly reactive free radicals. Moreover, upon termination of the isomerization process, the catalyst has to be removed by reduction and extraction. Metal hydrides such as Rh(I) hydride have also been used to catalyze the isomerization of alkenes (Cramer, J. Am. Chem. Soc., 88, 2272 (1966)). Additionally, metal carbonyls such as $Fe_3(CO)_{12}$ have been reported to afford isomerization of alkenes via a π-allyl complex (Casey et al., J. Am. Chem. Soc., 95, 2284 (1973)).

Cox, U.S. Pat. Nos. 5,545,792 and 5,789,645, describes the isomerization of 1-alkenes to internal alkenes in the presence of a catalyst composition comprising (I) alkyl aluminum alkoxide of the formula $R^3{}_n Al(OR^4)_p$ where $R^3$ and $R^4$ are alkyl radicals, n is in the range of from 0.75 to 1.85, p is in the range of from 1.15 to 2.25 and the sum of n and p is 3, and (ii) a cobalt salt of an organic carboxylic acid or reduced form thereof. It is stated in these patents that while the alkyl aluminum alkoxide can be formed by controlled oxidation of aluminum trialkyl in any known manner, e.g., by oxidation with air, a preferred method comprises the in situ formation of the alkyl aluminum alkoxide. To this end, suitable proportions of aluminum trialkyl and cobalt carboxylate are added to the isomerization reactor, whereby the alkyl aluminum alkoxide is generated in situ, presumably by oxygen atoms released from the cobalt carboxylate as it is reduced by the aluminum trialkyl.

U.S. Pat. No. 3,439,054 to Kroll describes a catalyst composition for the hydrogenation of olefinically unsaturated compounds. This catalyst composition comprises the reaction product of an Fe or Co carbonyl compound and an aluminum trialkyl or alkylaluminum hydride.

Internal alkenes find a number of commercial uses. They are, for example, used for the preparation of alkyl succinyl anhydride (ASA), a paper size, by reacting them with maleic anhydride. Internal alkenes are usually made by isomerization from the corresponding primary or 1-alkenes (also known as α-olefins), the latter compounds being available from refineries. The most common isomerization procedure for this purpose involves the use of acid catalysts. As already mentioned, the acid-catalyzed isomerization of alkenes also affords oligomers as side products. Oligomers, on the other hand, do not form adducts with maleic anhydride and, therefore, lower the effectiveness of the ASA paper size. Moreover, oligomers may also contribute to the formation of deposits in the paper mill. It would, thus be desirable to be able to isomerize 1-alkenes to internal alkenes without simultaneously producing substantial amounts of oligomers.

SUMMARY OF THE INVENTION

The present invention is directed to a process for the isomerization of 1-alkene to internal alkene wherein 1-alkene is combined, under isomerization conditions, with combinations of (I) salts of Group VIII transition metals such as nickel, cobalt, iron, palladium, platinum, rhodium and iridium and (ii) alkylaluminum compounds, particularly aluminum trialkyls and/or alkylaluminum halides, said combinations isomerizing the 1-alkene to internal alkene with only little formation of oligomers.

The present invention relates to a process for the isomerization of 1-alkene to internal alkene wherein 1-alkene is combined with a catalyst formed by contacting at least one Group VIII transition metal salt and at least one alkylaluminum compound. The process is conducted in liquid phase and at a temperature of from about 50 to about 200° C. If the at least one Group VIII transition metal salt includes cobalt and the at least one alkylaluminum compound includes trialkylaluminum compound the process is carried out in the substantial absence of alkoxyaluminum species.

With respect to the terms "combined" and "combinations" as used herein and in the appended claims in conjunction with the the components of the catalytic composition of the present invention it is to be understood that the exact structure of the catalytic species formed upon contact between the above components (i) and (ii) is not known. Without wishing to be bound to any theory, it is assumed that some kind of reaction (interaction) between these components takes place which eventually results in the formation of the catalytically active species.

While the 1-alkene subjected to the process of the present invention may have any number of carbon atoms (but of course not less than 4) it will usually have between about 5 and about 40 carbon atoms, preferably about 6 to about 30 carbon atoms and even more preferred about 10 to about 20 carbon atoms. The 1-alkene can either be an individual alkene or a mixture of two or more 1-alkenes.

The Group VIII transition metal will usually be selected from Ni, Co, Pd, Pt, Rh and Ir. Preferably it is at least one of Ni, Co and Pd, Co and Pd being the two most preferred Group VIII transition metals.

Preferred Group VIII transition metal salts contain halogen, especially chlorine, and/or chelate-forming ligand, such as acetylacetonate.

Alkylaluminum compounds for use in the present invention preferably are those of the general formula $AlR_a X_b$ in which R represents an alkyl radical, X represents a halogen radical, particularly chlorine, a is an integer of from 1 to 3, b is 0, 1 or 2, and the sum (a+b) is 3. The alkyl radicals R in the general formula above will usually have from 1 to about 40, particularly from 1 to about 10, and even more preferred 1 to about 6 carbon atoms. Specific examples of said alkyl radicals include methyl, ethyl, isopropyl, n-butyl, 2-butyl, isobutyl, n-pentyl and n-hexyl.

The value of a in the above general formula will usually be 2 or 3. Trialkylaluminum compounds (a=3) are preferred.

Examples of particularly preferred trialkylaluminum compounds for use in the present invention are trimethylaluminum, triethylaluminum and diethylaluminumchloride.

The molar ratio of 1-alkene to be isomerized to Group VIII transition metal(s) employed in the present process usually ranges from about 1:1 to about 10,000:1, more frequently from about 10:1 to about 5,000:1. Preferred ratios range from about 500:1 to about 4,000:1, particularly from about 700:1 to about 2,000:1.

The atomic ratio of Group VIII transition metal(s) to aluminum in the alkylaluminum compound(s) is generally in the range of from about 2:1 to about 1:500, more frequently from about 1:1 to about 1:300, with a range from about 1:2 to about 1:100 being even more preferred.

A preferred temperature at which the present isomerization is to be conducted is from about 80 to about 150° C., particularly from about 80 to about 120° C.

The present process can be carried out in the presence or absence of solvent. If a solvent is used it is suitably selected from optionally halogenated aliphatic and aromatic hydrocarbons, aliphatic ethers and combinations thereof.

The present invention also relates to a catalytic composition for the isomerization of 1-alkenes to internal alkenes. The catalytic composition is prepared by combining at least one Group VIII transition metal salt and at least one alkylaluminum compound of the general formula $AlR_aX_b$. R in the general formula represents an alkyl radical, X represents a halogen radical, a is an integer of from 1 to 3, b is 0, 1 or 2, and the sum (a+b) is 3. The Group VIII transition metal salt and the alkylaluminum compound are combined in a ratio sufficient to provide an atomic ratio of Al in the alkylaluminum compound(s) to Group VIII transition metal (s) of at least about 1:1. Moreover, if the at least one Group VIII transition metal salt includes cobalt and the at least one alkylaluminum compound includes trialkylaluminum compound the catalytic composition is substantially free of alkoxyaluminum species.

Preferred Group VIII transition metals and salts thereof and preferred alkylaluminum compounds for the preparation of the catalytic composition of the present invention are the same as those set forth above in connection with the present isomerization process. The same applies to the preferred atomic ratio of Group VIII transition metal(s) to Al in the alkylaluminum compound(s).

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

The process according to the present invention can successfully isomerize 1-alkenes to internal alkenes with little formation of oligomers, in contrast to the conventionally employed isomerization processes for alkenes. Moreover, whenever the starting 1-alkene(s) has/have at least 6 carbon atoms and, thus more than one internal alkene can be formed (e.g., 2-alkene, 3-alkene, 4-alkene, etc.) the predominant product will usually be the 2-alkene. In most cases the 2-alkene will account for at least about 50%, particularly at least about 60% and up to 70% or more of the internal alkenes formed; Also, if the Group VIII transition metal salt includes cobalt (or any other Group VIII transition metal) and the alkylaluminum compound includes trialkylaluminum compound, the isomerization proceeds smoothly even in the substantial absence of alkoxyaluminum species, in contrast to the disclosure of the U.S. patents to Cox discussed above, according to which a substantial percentage of the alkyl groups of the trialkylaluminum species must be converted to alkoxy groups in order to obtain a sufficiently high catalytic activity. In the present context the term "substantial absence" means that alkoxyaluminum species are preferably present, if at all, in only trace amounts and in any event in amounts which afford a ratio of alkoxy groups bonded to Al to alkyl groups bonded to Al (in the alkylaluminum compound(s)) that is not higher than 0.1:1, preferably not higher than 0.05:1 and most preferred not higher than 0.01:1. Such low ratios can easily be accomplished by keeping the presence of oxygen (air) during the isomerization at a minimum and excluding the presence of other oxygen-containing species (e.g. anions in the transition metal salt(s)) that might cause oxidation of alkylaluminum compound to alkoxyaluminum species. In order to exclude molecular oxygen it is preferred to purge both the reactor and the starting materials (1-alkene, transition metal salt, solvent etc.) with an inert gas such as nitrogen or argon and to conduct the isomerization in an inert gas atmosphere.

The starting materials for the process of the present invention are 1-alkenes having at least 4 carbon atoms. Generally the 1-alkenes employed in the process of the present invention will have about 5 to about 40, more frequently about 6 to about 30 carbon atoms, although there is no upper limit for the number of carbon atoms from a practical point of view, the number of carbon atoms being primarily determined by the intended use of the desired internal alkenes. Alkenes of about 10 to about 20 carbon atoms (e.g., 26–20 carbon atoms) are particularly desirable substrates for the process of the present invention if the resulting internal alkenes are to be used for the production of ASA.

The 1-alkene to be isomerized by the process of the present invention may be linear or branched and may also contain a cycloaliphatic or aromatic ring structure. Specific examples of 1-alkenes that can successfully be subjected to the isomerization process of the present invention are 1-pentene, 3-methyl-1-butene, 2-methyl-1-pentene, 4-methyl-1-pentene, 1-hexene, 1-heptene, 1-octene, 2-methyl-1-octene, 2-ethyl-1-hexene, 5-methyl-1-heptene, 1-nonene, 1-decene, 1-undecene, 1-dodecene, 2-methyl-1-dodecene, 1-tetradecene, 2-methyl-1-tetradecene, 1-hexadecene, 2-methyl-1-hexadecene, 5-methyl-1-hexadecene, 1-octadecene, 2-methyl-1-octadecene, 1-eicosene, 2-methyl-1-eicosene, 1-docosene, 1-tetracosene, 1-hexacosene, vinylcyclohexane and 2-phenyl-1-butene, although the present invention is in no way limited to these examples.

It is, of course, also possible to isomerize more than one 1-alkene at the same time. For example, mixtures of two, three, four, five, six and more 1-alkenes can be employed as starting material of the process of the present invention. Moreover, it is not necessary that the 1-alkenes be employed in a substantially pure or purified form. Rather, they can be employed as mixture (or contaminated) with one or more other compounds which are not 1-alkenes, provided said other compounds do not substantially interfere with the isomerization. Typical examples of other compounds which may (and often will) be present in the starting material (1-alkene) are internal alkenes as well as saturated (cyclo) aliphatic and aromatic hydrocarbons.

The metals of the transition metal salts for use in the present invention are cobalt, nickel, iron, palladium, platinum, osmium, iridium, rhodium and ruthenium. Of these cobalt, nickel, palladium, platinum, osmium and iridium are preferred metals. Particularly in view of the activity of the resulting catalytic species, cobalt, palladium and nickel are even more preferred. The most preferred metals for use in the present invention are cobalt and palladium, particularly cobalt, the latter also offering the advantage of a comparatively low price. Two or more of these metals can be employed in combination, for example in the form of two or more different transition metal salts.

The anions or ligands, respectively of the Group VIII transition metal salts are not particularly limited. Said anions (ligands) can be both inorganic and organic. Examples thereof include halides (e.g., fluorides, chlorides, bromides and iodides), sulfate, nitrate, phosphate, carbonate, carboxylates such as formate, acetate, propionate, oxalate, benzoate, phthalate and naphthoate, chelating agents like acetylacetonate and EDTA, as well as cycloalkadienyl ligands like 1,5-cyclooctadienyl and pentadienyl (metallocenes) etc. Of course, two or more different anions (ligands) may be present, both in the form of a single metal salt and in the form of mixtures of salts (optionally of different metals). Particularly desirable anions (ligands) for the purposes of the present invention are the halides, particularly chloride and bromide and especially chloride, and acetylacetonate. Specific examples of corresponding salts for use in the present invention are Ni(II) chloride, Ni(II) acetylacetonate, Co(III) acetylacetonate, $PdCl_2$, $PtCl_2$(cyclooctadienyl)$_2$, Ir(III) acetylacetonate and Rh(III) acetylacetonate. Those skilled in the art will recognize that there are many more other salts that can be used for the purposes of the present invention.

According to the present invention an alkylaluminum compound is used in combination with the Group VIII transition metal salt for interaction with the latter, and thereby generation of catalytically active species for the isomerization of 1-alkene to internal alkene.

The alkylaluminum compound for use in the present invention is not particularly limited, as long as it contains at least one alkyl group directly bonded to an aluminum atom. However, a particularly suitable class of alkylaluminum compounds is that of the general formula $AlR_aX_b$, in which R represents an alkyl radical, X represents a halogen radical, a is an integer of from 1 to 3, b is 0, 1 or 2, and the sum (a+b) is 3.

In the above general formula the alkyl group(s) R can have any number of carbon atoms, although a range of 1 to about 40 carbon atoms per alkyl group is preferred from a practical point of view. Thus, if "a" in the above formula is 3, the corresponding alkylaluminum compound preferably contains a total of not more than about 120, more preferred not more than about 100 carbon atoms. A relatively high total number of carbon atoms may be preferred in cases where the volatility of the alkylaluminum compound should be kept as low possible (e.g., if the isomerization is to be conducted with a relatively high-boiling alkene at a relatively high temperature and under atmospheric pressure). Alkyl groups with a high number of carbon atoms may also be of advantage if at the end of the isomerization the catalyst is to be deactivated (destroyed) by the addition of water, resulting, i.a., in the hydrolytic cleavage of the alkyl-Al bond and the generation of the corresponding alkane. If said alkane has a substantially higher boiling point than the alkene(s) present in the reaction medium the separation of the latter from the former by, e.g., distillation is facilitated.

Typically, however, the alkyl group(s) of the alkylaluminum compound will have from 1 to about 10, and particularly from 1 to about 6 carbon atoms. An upper limit of 6 carbon atoms may be particularly desirable in cases where the alkenes are relatively high-boiling and the catalyst is to be deactivated by addition of water. This addition of water would then result in the liberation of a relatively low-boiling hydrocarbon (e.g. methane, ethane, hexane etc.) from the alkylaluminum compound which, in turn, would facilitate separation or removal thereof by distillation.

The alkyl groups R for use in the alkylaluminum compounds can be linear or branched and, for $a \geq 2$, may be identical or different (usually they are identical). Specific examples thereof are methyl, ethyl, propyl, isopropyl, n-butyl, isobutyl, 2-butyl, n-pentyl, n-hexyl, n-heptyl, 2-ethylhexyl, n-octyl, n-nonyl and n-decyl. Preferred groups R for use in the present invention include methyl, ethyl, n-propyl, isopropyl, n-butyl, 2-butyl, isobutyl, n-pentyl and n-hexyl. Most preferred are methyl and ethyl (also in view of price and availability of corresponding compounds).

Preferred values of "a" in the above general formula are 2 and 3, particularly 3. In other words, preferred alkylaluminum compounds for use in the present invention are trialkylaluminum compounds such as trimethylaluminum and triethylaluminum, as well as tributylaluminum, triisobutylaluminum, diethylisobutylaluminum, trihexylaluminum, triheptylaluminum, and trioctylaluminum.

If "b" in the above formula is 1 or 2, i.e., one or two halogen radicals X are present, X is preferably selected from Cl and Br and is most preferably Cl. A preferred representative of the class of alkylaluminum halides for use in the present invention is diethylaluminumchloride (DEAC). Preferred further examples thereof include ethylaluminumdichloride and isobutylaluminumdichloride.

While preferred alkylaluminum compounds for use in the present invention have been set forth above it is to be understood that the present invention is not limited to the use of those compounds. Examples of the numerous other compounds that can be used as alkylaluminum compounds in the present invention are ethylaluminum sesquichloride and isobutylaluminum sesquichloride. Generally, the most suitable alkylaluminum compound(s) for use in the present invention do not contain any atoms other than aluminum, carbon, hydrogen and, optionally, halogen.

Regarding the relative amounts of 1-alkene(s), Group VIII transition metal salt(s) and alkylaluminum compound (s) used in the process of the present invention, said amounts can vary over very broad ranges. In practice, however the molar ratio of 1-alkene to Group VIII transition metal will generally be in the range of from about 1:1 to about 10,000:1, more often from about 10:1 to about 5,000:1. A molar ratio of from about 500:1 to about 4,000:1 and particularly from about 700:1 to about 2,000:1 will often be the most desirable for the purposes of the present invention.

The atomic ratio of Group VIII transition metal to Al in the alkylaluminum compound will usually range from about 2:1 to about 1:500, particularly from about 1:1 to about 1:300, with a range from about 1:2 to about 1:100 being most common. A very high excess of Al over Group VIII transition metal does not offer any particular advantages. On the other hand, too little Al relative to transition metal may sometimes have an adverse effect on the activity of the catalytic system. At any rate, the optimum ratios of 1-alkene, Group VIII transition metal and alkylaluminum compound depend to a large extent on the specific compounds to be employed and can readily be determined by the person of ordinary skill in the art by means of routine experimentation.

The process of the present invention is suitably carried out at a temperature from about 50 to about 200° C., preferably at a temperature of from about 80 to about 150° C., and particularly about 80 to about 120° C. The temperature to be employed is mainly determined by such factors as activity of the catalytic system, desired reaction time and boiling points (and decomposition temperatures) of the species present in the isomerization medium. Apparently the rate of isomerization will increase with increasing temperature. Higher temperatures will, on the other hand also accelerate undesirable side reactions such as catalyst decomposition and oligomerization and polymerization of the alkenes present. Finally, it should also be taken into account that too high a process temperature may make it necessary, due to the boiling points of the components present, to work under superatmospheric pressure which, although possible, generally increases the overall cost of the process. Therefore, it will usually be most desirable to be able to operate at the minimum temperature that still affords an acceptable rate of isomerization.

Typical reaction times for the process of the present invention range from about 1 to about 12 hours, particularly from about 2 to about 6 hours and even more typical from about 2 to about 4 hours (for batch processes). The reaction time is, of course, determined by such factors as activity of the catalyst, catalyst concentration, process temperature and desired degree of conversion. Regarding the last factor, it may not always be necessary to achieve degrees of isomerization close to 100% or even close to 90%. Preferably, however the present isomerization is allowed to proceed until a degree of isomerization of at least about 70% is reached.

As already mentioned, the process of the present invention can be carried out at superatmospheric pressure. Apparently it is more convenient, and thus preferred, to be able to operate at atmospheric pressure. However, certain combinations of temperatures necessary for achieving an acceptable rate of isomerization on the one hand and boiling points of one ore more of the components of the reaction medium on the other hand may sometimes make it unavoidable to use higher than atmospheric pressure.

The process of the present invention can be carried out both in the presence and absence of solvent. While it will usually be preferred to use no solvent, it may in some situations be advisable or even necessary to work in the presence of solvent. For example, if the amount of liquid (and particularly alkene) present is not sufficient to accommodate (dissolve or at least disperse) the (solid or liquid) components of the catalytic system and to afford a not too viscous liquid phase, a solvent or solvent mixture may have to be added. The solvent used should have a boiling point that is above the temperature under which the isomerization is to be carried out. Also, if at the end of the process the isomerized alkene is to be separated from the solvent by distillation, care should be taken that the boiling point difference between solvent and alkene is sufficiently large to not unnecessarily complicate said distillation. The solvent should also be miscible with at least the 1-alkene and should not interfere with the isomerization process, particularly not react with any of the other species present. Especially in view of the presence of alkylaluminum compound, the solvent should, of course, not include any active hydrogen atoms that can react with components of the catalytic system (e.g., alkylaluminum compound). Examples of suitable solvents for use in the present invention are non-polar solvents such as optionally halogenated (particularly chlorinated), aliphatic, cycloaliphatic and aromatic hydrocarbons and aliphatic ethers. These solvents suitably have a boiling point between about 80 and about 200° C., particularly about 100 and 150° C. Specific examples thereof are toluene, the xylenes, chlorobenzene, the dichlorobenzenes, chloroform, carbon tetrachloride, octane, decane, and dodecane as well as mixtures of two or more of these solvents.

Particularly due to the sensitivity (reactivity) of most alkylaluminum compounds towards oxygen and water the process of the present invention should be carried out in the substantial absence of water (moisture) and molecular oxygen. To this end it is recommendable to purge the reactor with an inert dry gas such as nitrogen or argon before charging it and to also dry and deoxygenate the starting materials (including alkene, components of the catalytic system and solvent, if used) in conventional manner before introducing them into the isomerization reactor. Remaining traces of oxygen and water in the isomerization medium will usually be scavenged by reaction with alkylaluminum compound. Of course, it is also highly preferred to as much as possible limit the access of molecular oxygen and water (moisture) to the liquid medium during the isomerization process. Therefore the present process should be carried out in an inert atmosphere, e.g., under dry nitrogen gas.

While the components of the isomerization catalyst according to the present invention can be combined in any manner which allows interaction thereof with formation of the catalytically active species, a particularly convenient and, thus preferred way is the generation of the catalyst in situ, i.e., inside the isomerization medium. This can simply be accomplished by adding the components of the catalytic system separately to the isomerization reactor. The order and form of addition of the alkene, catalyst components, solvent etc. to the reactor is, however, not critical for the successful operation of the process of the present invention. Moreover, additional reagents and components for the isomerization reaction beyond those set forth above are not necessary and should thus preferably not be present.

The process of the present invention can be carried out batchwise, semicontinuously and continuously. For continuous operation a tubular reactor may, for example, be used.

At the end of the isomerization the alkene may be separated from the remaining components in any conventional manner such as, e.g., by filtration, distillation, extraction and combinations thereof. In some cases it may be desirable to first convert the alkylaluminum compound into a less moisture-sensitive compound, e.g., by careful addition of water to the isomerization medium. Especially with the more expensive transition metals it will also be necessary for economic reasons to recover the metal values and to optionally recycle them to the process.

The process according to the present invention is particularly suitable for producing internal alkenes which contain at least about 50 mole-%, particularly at least 60 mole-% and up to 70 or more mole-% of 2-alkene(s) (if the starting 1-alkene(s) contained at least 6 carbon atoms). It is also advantageous in that generally less than about 5%, often less than about 2%, of the alkene initially employed will become oligomerized.

EXPERIMENTS

In the Examples the following materials were employed:
Alkenes
NEODENE 2024, a mixture of 1-alkenes having 20, 22 and 24 carbon atoms, obtained from Shell Chemicals and used as received.

NEODENE 18, a mixture of 1-alkenes having 18 carbon atoms, obtained from Shell Chemicals and used as received.

The following materials were purchased from Aldrich and used as received.

Transition Metal Salts

Ni(II) chloride (purity 98%), Ni(II) acetylacetonate (purity 98%)

Fe(III) acetylacetonate, Fe(II) acetate, Na Fe(III) EDTA

Pd(II) chloride

Co(III) acetylacetonate

Rh(II) acetylacetonate (purity 97%)

Ir(III) acetylacetonate

Pt(II) chloride COD (COD=1,5-cyclooctadienyl)

Solvent

Toluene (reagent grade)

All experiments were carried out under a nitrogen atmosphere.

EXAMPLE 1

A mixture of Ni(II) chloride (0.1 g, 0.7 mmol), NEODENE 2024 (5.0 g, 15 mmol), trimethylaluminum (2 mmol), and toluene (30 ml) is heated for 4 hours at 50° C. According to $^1$H-NMR analysis the degree of isomerization is 100%.

EXAMPLE 2

A mixture of Ni(II) acetylacetonate (0.2 mmol), NEODENE 2024 (15 mmol), trimethylaluminum (3 mmol) and toluene (25 ml) is heated for 9 hours at 120° C. The resulting degree of isomerization is 94%.

EXAMPLE 3

A mixture of NEODENE 18 (19.2 g, 76 mmol), Co(III) acetylacetonate (40 mg, 0.1 mmol), and trimethylaluminum (0.2 mmol) is heated for 3 hours at 100° C. Analyses by $^1$H-NMR, $^{13}$C-NMR and gas chromatography show that 96% of internal alkene are present, with the following distribution: 59% 2-alkene, 20% 3-alkene, 8% 4-alkene, 11% 5- and higher alkene. 0.5% of the alkene are present as dimer. Trimer is not observed.

EXAMPLE 4

A mixture of NEODENE 18 (7.7 g, 31 mmol), Co(III) acetylacetonate (7 mg, 0.02 mmol), and trimethylaluminum (0.2 mmol) is heated for 5 hours at 120° C. Analysis by $^1$H-NMR shows a degree of isomerization of 97%.

EXAMPLE 5

A mixture of NEODENE 2024 (5.0 g, 15 mmol), Pd(II) chloride (36 mg, 0.2 mmol), trimethylaluminum (3 mmol), and toluene (10 ml) is heated for 17 hours at 120° C. The resulting degree of isomerization is 96%.

EXAMPLE 6

A mixture of NEODENE 2024 (5.0 g, 15 mmol), Fe(III) acetylacetonate (0.2 mmol), trimethylaluminum (3 mmol), and toluene (25 ml) is heated for 14 hours at 120° C. Analysis by $^1$H-NMR shows a degree of isomerization of 14%.

EXAMPLE 7

A mixture of NEODENE 2024 (5.0 g, 15 mmol), Na Fe(III)EDTA (0.2 mmol), and trimethylaluminum (6 mmol) is heated for 40 hours at 120° C. Analysis by $^1$H-NMR shows a degree of isomerization of 64%.

EXAMPLE 8

A mixture of NEODENE 18 (19.2 g, 76 mmol), Pt(II) chloride COD (0.02 mmol), and trimethylaluminum (3 mmol) is heated for 10 hours at 120° C. The resulting degree of isomerization is 87%.

EXAMPLE 9

A mixture of NEODENE 2024 (10.0 g, 30 mmol), Rh(III) acetylacetonate (160 mg, 0.4 mmol), and trimethylaluminum (1 mmol) is heated for 3 hours at 120° C. The resulting degree of isomerization is 97%.

EXAMPLE 10

A mixture of NEODENE 2024 (5.0 g, 15 mmol), Ir(III) acetylacetonate (0.02 mmol), and trimethylaluminum (6 mmol) is heated for 2 hours at 120° C. The resulting degree of isomerization is 100%.

EXAMPLE 11

A mixture of NEODENE 18 (23.0 g, 91 mmol), Co(III) acetylacetonate (21 mg, 0.06 mmol), and diethylaluminumchloride (1.5 mmol) is heated for 3 hours at 120° C. The resulting degree of isomerization is 99%.

Application Example

A mixture of maleic anhydride (0.3 mol) and phenothiazine (175 ppm) in the molten state (temperature>60° C.) is added dropwise to a heated (198° C.) liquid isomerized olefin similar to that produced in Example 3 above (0.5 mol) over a period of three hours. The reaction is allowed to proceed at 215° C. for three hours. After cooling down to room temperature, the entire reaction mixture is subjected to vacuum stripping to remove unreacted maleic anhydride and excess olefin. Thereby a liquid is obtained in a yield of 88% based on the amount of maleic anhydride originally employed. This liquid contains 92% by weight of alkylsuccinic anhydride.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A process for the isomerization of 1-alkene to internal alkene, wherein 1-alkene is combined, in liquid phase and at a temperature of from about 50 to about 200° C., with unsupported catalyst formed by contacting at least one Group VIII transition metal salt and at least one alkylaluminum compound, provided that if the at least one Group VIII transition metal salt includes cobalt and the at least one alkylaluminum compound includes trialkylaluminum compound the process is carried out in the substantial absence of alkoxyaluminum species.

2. The process of claim 1, wherein the 1-alkene contains about 5 to about 40 carbon atoms.

3. The process of claim 2, wherein the 1-alkene contains about 6 to about 30 carbon atoms.

4. The process of claim 3, wherein the 1-alkene contains about 10 to about 20 carbon atoms.

5. The process of claim 1, wherein the 1-alkene is a mixture of at least two 1-alkenes.

6. The process of claim 1, wherein the Group VIII transition metal is selected from Ni, Co, Pd, Pt, Rh and Ir.

7. The process of claim 6, wherein the Group VIII transition metal is selected from Ni, Co and Pd.

8. The process of claim 7, wherein the Group VIII transition metal includes at least one of Co and Pd.

9. The process of claim 1, wherein the at least one Group VIII transition metal salt includes halogen.

10. The process of claim 9, wherein the halogen includes chlorine.

11. The process of claim 1, wherein the at least one Group VIII transition metal salt includes a chelate-forming ligand.

12. The process of claim 11, wherein the chelate-forming ligand includes acetylacetonate.

13. The process of claim 1, wherein the at least one alkylaluminum compound includes a compound of the general formula $AlR_aX_b$, in which R represents an alkyl radical, X represents a halogen radical, a is an integer of from 1 to 3, b is 0, 1 or 2, and the sum (a+b) is 3.

14. The process of claim 13, wherein the radical R represents alkyl of from 1 to about 40 carbon atoms.

15. The process of claim 14, wherein the radical R represents alkyl of from 1 to about 10 carbon atoms.

16. The process of claim 15, wherein the radical R represents alkyl of from 1 to about 6 carbon atoms.

17. The process of claim 16, wherein the radical R is selected from methyl, ethyl, n-propyl, isopropyl, n-butyl, 2-butyl, isobutyl, n-pentyl and n-hexyl.

18. The process of claim 13, wherein a is 2 or 3.

19. The process of claim 18, wherein a is 3.

20. The process of claim 13, wherein X includes Cl.

21. The process of claim 1, wherein the at least one alkylaluminum compound includes a compound selected from trimethylaluminum, triethylaluminum and diethylaluminumchloride.

22. The process of claim 21, wherein the at least one alkylaluminum compound includes trimethylaluminum.

23. The process of claim 1, wherein the at least one Group VIII transition metal salt includes at least one compound selected from Ni(II) chloride, Ni(II) acetylacetonate, Co(III) acetylacetonate, $PdCl_2$, $PtCl_2(cyclooctadienyl)_2$, Ir(III) acetylacetonate and Rh(III) acetylacetonate.

24. The process of claim 1, wherein the molar ratio of 1-alkene to Group VIII transition metal is from about 1:1 to about 10,000:1.

25. The process of claim 24, wherein the molar ratio is from about 10:1 to about 5,000:1.

26. The process of claim 25, wherein the molar ratio is from about 500:1 to about 4,000:1.

27. The process of claim 26, wherein the molar ratio is from about 700:1 to about 2,000:1.

28. The process of claim 1, wherein the atomic ratio of Group VIII transition metal(s) to Al in the alkylaluminum compound(s) is from about 2:1 to about 1:500.

29. The process of claim 28, wherein the atomic ratio is from about 1:1 to about 1:300.

30. The process of claim 29, wherein the atomic ratio is from about 1:2 to about 1:100.

31. The process of claim 1, which is carried out at a temperature from about 80 to about 150° C.

32. The process of claim 31, which is carried out at a temperature from about 80 to about 120° C.

33. The process of claim 1, which is carried out in the presence of solvent.

34. The process of claim 33, wherein the solvent is selected from aliphatic and aromatic hydrocarbons, halogenated aliphatic and aromatic hydrocarbons, aliphatic ethers and mixtures thereof.

35. The process of claim 1, which is carried out in the absence of solvent.

36. The process of claim 1, which is carried out under substantially anhydrous conditions.

37. The process of claim 1, which is carried out in the substantial absence of molecular oxygen.

38. The process of claim 1, wherein the catalyst is formed in situ.

39. The process of claim 1, wherein the predominant isomerization product is 2-alkene.

40. The process of claim 39, wherein the starting 1-alkene (s) contain(s) more than 5 carbon atoms and 2-alkene accounts for at least about 50 mole-% of the internal alkenes formed.

41. The process of claim 1, which affords less than about 5% of oligomer as side product.

42. The process of claim 1, wherein at least one 1-alkene having from 6 to 30 carbon atoms is contacted, at a temperature from about 80 to about 150° C. and under substantially anhydrous conditions and in the substantial absence of molecular oxygen, with at least one Group VIII transition metal salt selected from chlorides and acetylacetonates of Ni, Co and Pd and with at least one alkylaluminum compound selected from trimethylaluminum, triethylaluminum and diethylaluminumchloride, the molar ratio of 1-alkene(s) to Group VIII transition metal(s) being from about 100:1 to about 2,000:1, and the atomic ratio of Group VIII transition metal(s) to Al in the alkylaluminum compound(s) being from about 1:2 to about 1:100, thereby forming internal olefin comprised of at least about 60 mole-% of 2-alkene(s), without concurrent formation of more than about 5% of oligomers.

43. A process for the isomerization of 1-alkene to internal alkene, wherein 1-alkene containing at least 5 carbon atoms is combined, in liquid phase and at a temperature of from about 50 to about 200° C., with a catalyst formed by contacting at least one Group VIII transition metal salt and at least one trialkylaluminum compound, provided that if the at least one Group VIII transition metal salt includes cobalt the process is carried out in the substantial absence of alkoxyaluminum species.

44. The process of claim 43, wherein the Group VIII transition metal is selected from Co, Pd, Pt, Rh and Ir.

45. The process of claim 45, wherein the at least one Group VIII transition metal salt comprises at least one compound selected from Ni(II) chloride, Co(III) acetylacetonate, $PdCl_2$, $PtCl_2(cyclooctadienyl)_2$, Ir(III) acetylacetonate and Rh(III) acetylacetonate.

46. The process of claim 44, which affords less than about 5% of oligomer as side product.

47. A process for the isomerization of 1-alkene to internal alkene, wherein 1-alkene containing at least 5 carbon atoms is combined, in liquid phase and at a temperature of from about 50 to about 200° C., with a catalyst formed by contacting at least one salt of a Group VIII transition metal selected from cobalt, iron, palladium, platinum, osmium, iridium, rhodium and ruthenium and at least one alkylaluminum compound, provided that if the at least one Group VIII transition metal salt includes cobalt and the at least one alkylaluminum compound includes trialkylaluminum compound the process is carried out in the substantial absence of alkoxyaluminum species; wherein the predominant isomerization product is 2-alkene.

48. The process of claim 47, wherein the Group VIII transition metal comprises at least one of Co and Pd.

49. The process of claim 47, wherein the at least one Group VIII transition metal salt comprises at least one compound selected from Co(III) acetylacetonate, $PdCl_2$, $PtCl_2(cyclooctadienyl)_2$, Ir(III) acetylacetonate and Rh(III) acetylacetonate.

* * * * *